(12) United States Patent
Belmonte et al.

(10) Patent No.: US 7,485,746 B2
(45) Date of Patent: Feb. 3, 2009

(54) STAGED COUNTERCURRENT OXIDATION

(75) Inventors: Frank G. Belmonte, Hawthorn Woods, IL (US); David L. Sikkenga, Wheaton, IL (US); Olusola Sunday Ogundiran, League City, TX (US); Kenneth J. Abrams, Naperville, IL (US); Linus Kai-Wah Leung, Naperville, IL (US); Christopher G. Meller, Carol Stream, IL (US); Dale A. Figgins, Houston, TX (US); Allen B. Mossman, Wheaton, IL (US)

(73) Assignee: BP Corporation North America Inc., Warrenville, IL (US)

( * ) Notice: Subject to any disclaimer, the term of this patent is extended or adjusted under 35 U.S.C. 154(b) by 527 days.

(21) Appl. No.: 10/713,660

(22) Filed: Nov. 14, 2003

(65) Prior Publication Data

US 2005/0107630 A1    May 19, 2005

(51) Int. Cl.
*C07C 51/255* (2006.01)

(52) U.S. Cl. .................. 562/413; 562/414; 562/416
(58) Field of Classification Search .................. 562/413, 562/416, 414
See application file for complete search history.

(56) References Cited

U.S. PATENT DOCUMENTS

| 2,962,361 | A | * | 11/1960 | Spiller, Jr. et al. | ........... 422/193 |
| 3,092,658 | A | * | 6/1963 | Baldwin et al. | ............. 562/413 |
| 3,406,196 | A | * | 10/1968 | Sebelist et al. | ............. 562/413 |
| 2001/0007910 | A1 | * | 7/2001 | Housley et al. | ............. 562/414 |

* cited by examiner

*Primary Examiner*—Taylor Victor Oh
(74) *Attorney, Agent, or Firm*—Kelly L. Cummings (57) ABSTRACT

A process for oxidation with oxygen of at least one aromatic hydrocarbon having oxidizable, substituents that maximizes the utilization of oxygen without reduction in the quality of the carboxylic acid products produced by means of a stage-wise countercurrent oxidation system is disclosed.

24 Claims, 3 Drawing Sheets

STAGED COUNTERCURRENT OXIDATION

FIELD OF THE INVENTION

This invention relates generally to an improved oxidation process for the conversion of one or more aromatic hydrocarbon materials having oxidizable substituents to their corresponding acid derivatives, and relates more particularly to such a process involving staged oxidation and recycle of residual oxygen from a second oxidation stage to a first oxidation stage.

BACKGROUND OF THE INVENTION

It is well known that aromatic hydrocarbons having at least one and preferably two or more oxidizable substituent groups may be converted into carboxylic acid products by effecting oxidation of such groups with molecular oxygen under controlled conditions. Such conditions have generally included the use of a known oxidation catalyst together with a suitable solvent.

During the present commercial production of aromatic acids such as terephthalic acid, it is essential that reactor oxygen partial pressure in the oxidation of an alkylaromatic be high enough to prevent oxygen starvation. A high oxygen partial pressure reduces the formation of undesirable colored by-products by suppressing coupling reactions. Also, a high partial pressure increases oxidation reaction rates, which allows higher reactor throughputs, and reduces the burning of the reaction solvent. However, in a commercial operation of such an oxidation system a significant loss of oxidation capacity occurs as a result of insufficient utilization of molecular, oxygen. It is therefore highly desirable to improve utilization of the oxygen and thereby to improve process efficiency and debottleneck and increase the rated capacity of an aforesaid commercial oxidation system and simultaneously to maintain the high quality of the carboxylic acid products produced.

Spillar et al., U.S. Pat. No. 2,962,361 (Nov. 29, 1960) discloses a stagewise continuous countercurrent oxidation system that "enables practically quantitative oxygen utilization . . . without substantial detriment to product yield or quality." The highest oxygen concentration is introduced at the final stage, and the off-gases from each stage are returned to the preceding stage while the partially oxidized products move from the first stage to the final stage. It is disclosed as desirable that the final oxidation stage be at the highest temperature, pressure and oxygen concentration. It is also disclosed with regard to the first oxidation stage 11 and the vent line 26 from it in FIG. 2 that "additional air or oxygen may be introduced through line 41 . . . for preventing the oxygen concentration in receiver 24, condenser 23 or line 26 from exceeding 8 volume percent (it is preferably zero)." Baldwin et al., U.S. Pat. No. 3,092,658 (Jun. 4, 1963) discloses a stagewise continuous countercurrent oxidation system that is very similar to that in aforesaid U.S. Pat. No. 2,962,361.

Baldwin, U.S. Pat. No. 3,064,044 (Nov. 13, 1962) also discloses a staged-countercurrent oxidation system. The uncondensed off-gases leaving the second oxidation stage are returned to the first oxidation stage, and the patent states should contain less than 8 percent oxygen but it may contain about 1 to 8 percent oxygen and hence it is introduced by lines 14 and 15 to supply oxygen in vessel 11. With regard to the first oxidation stage 11 and the condenser 20 and receiver 21 through which its off-gases pass, the patent also states that "the amount of additional air introduced from line 15 should be controlled so that the oxygen content of gases in condenser 20 and receiver 21 will be less than 8 percent, preferably near zero."

June et al., U.S. Pat. No. 6,153,790 (Nov. 28, 2000) discloses a process for producing diacid substituted aromatics with a purity of at least 97%. The process comprises contacting in a stirred tank reactor a dialkyl substituted aromatic in an organic acid solvent with an oxidant containing at least 50% by volume of oxygen at an oxygen partial pressure of at least 1 psia, at a temperature between about 176° F. and about 266° F., in the presence of a catalyst system comprising zirconium and cobalt. A vapor stream comprising the organic acid solvent, water vapor and unreacted oxidant is withdrawn from the reactor. More than 50% by volume of oxygen in the oxidant is required so that the total pressure of the reaction system can be low enough to allow reflux cooling of the reaction system at temperatures between about 176° F. and about 266° F. as a result of vaporization of liquid phase components to form the aforesaid vapor stream. The reactor design must effectively provide for nearly complete oxygen consumption below the liquid/gas interface. Nitrogen can be introduced in the vicinity of the liquid/gas interface in a quantity sufficient to render the vapor phase gas mixture nonflammable. The patent discloses that, if desired, after dilution with nitrogen, the unconsumed oxygen can be contacted with feed streams in an optional pre-reactor to provide nearly or fully complete utilization of oxygen.

Turner and Hously, U.S. patent application No. U.S. 2001/0007910 A1 published Jul. 12, 2001; PCT/US01/20109 published Jul. 18, 2002 as WO 02/055468 A1; PCT/US01/00825 published Jul. 19, 2001 as WO 01/51442 A2; and PCT/US01/19960 published Jul. 18, 2002 as WO 02/055467, disclose a process for the staged catalytic liquid phase, air oxidation of a suitable precursor, such as paraxylene, to a carboxylic acid, such as terephthalic acid, comprising oxygenating a feed stream comprising acetic acid and an oxidation catalyst at an elevated pressure of from 2000 up to 20,000 kPa, continuously and simultaneously feeding the oxygenated feed stream and paraxylene to a first reaction zone that is positioned upstream from a conventional oxidation reactor to form a reaction medium in which the acetic acid to paraxylene mass ratio is in the range of from 10:1 to 20:1 and the reaction products are maintained in solution. In this first reactor the uptake of oxygen within the reaction medium in the first reaction zone is limited to less than 50% of the oxygen for full conversion of the paraxylene present to terephthalic acid. Thereafter, the reaction medium is fed from the first oxidation zone to the aforesaid conventional oxidation reactor and simultaneously the pressure of the reaction medium is reduced to a pressure in the range of from 1000 to 2,000 kPa in the conventional oxidation reactor. In WO 01/51442 A2 the process is disclosed as being a method for increasing the production capacity of a conventional oxidation reactor, while the three other patent publications disclose it as a method for reducing the formation of impurities in the final carboxylic acid product and for controlling degradation of the solvent and precursor.

Although it is highly desirable to maximize the utilization of oxygen and thereby improve process efficiency and increase the rated capacity of a commercial oxidation system while maintaining the high quality of the carboxylic acid products produced and without the need of adding additional compressor capacity, that goal has never been achieved and the means for achieving it has never been disclosed.

SUMMARY OF THE INVENTION

The present invention is an improved continuous staged countercurrent process of this invention for the catalytic oxidation of at least one benzene disubstituted with oxidizable substituents selected from the class consisting of alkyl, hydroxyalkyl, aldehyde, carboxy groups and mixtures thereof, to its corresponding acid derivative in a solvent system. This process comprises the steps of: (a) introducing into a first oxidation zone a feed mixture comprising from about 7 to about 60 weight percent of the total amount of at least one disubstituted benzene introduced in steps (a) and (d) and at least a portion of the total amounts to be introduced in steps (a) and (d) of each of (i) the solvent, (ii) catalyst components comprising at least one catalytic metal selected from the class consisting of manganese, cobalt, nickel, zirconium, hafnium, cerium and mixtures thereof, and (iii) bromine at a mole ratio based on total catalytic metals within the range of from about 1:20 to about 5:1; (b) partially oxidizing the disubstituted benzene in the first oxidation stage with a molecular oxygen-containing gas initially containing from about 3 to about 20 volume percent of molecular oxygen, at a temperature in the range of from about 250° F. to about 401° F., and with the relative amounts of disubstituted benzene, catalyst components, and solvent and with the temperature being such that from about 25 to about 99.95 weight percent of the disubstituted benzene fed to the first oxidation stage is oxidized to form a gas mixture comprising unreacted molecular oxygen and vaporized solvent and a first product mixture comprising unreacted disubstituted benzene, partially oxidized disubstituted benzene, acid derivative product, and solvent, and at a pressure that is sufficient to maintain the disubstituted benzene, partially oxidized disubstituted benzene, acid derivative product, and solvent substantially as a liquid phase or a solid-liquid slurry and such that the concentration of residual molecular oxygen in the remaining gas mixture is from about 0.3 to about 2 volume percent; (c) recovering the resulting first product mixture from the first oxidation stage and feeding at least a portion of the recovered first product mixture to a second oxidation stage; (d) feeding to the second oxidation stage molecular oxygen or a molecular oxygen-containing gas and the remainder, if any, of the aforesaid predetermined total amounts introduced in steps (a) and (d) of disubstituted benzene, catalyst components, solvent and bromine; (e) substantially completely oxidizing in the second oxidation stage the partially oxidized disubstituted benzene and unreacted disubstituted benzene fed to the second oxidation stage in the presence of molecular oxygen-containing gas at a temperature within the range of from about 347° F. to about 421° F. and with the relative amounts of disubstituted benzene, partially oxidized disubstituted benzene, catalyst components and solvent and with the temperature being such that from about 96 to about 100 weight percent of the disubstituted benzene and partially oxidized disubstituted benzene are oxidized to form a second product mixture comprising the aforesaid acid derivative product and solvent, and at a pressure sufficiently high to maintain the acid derivative product, partially oxidized disubstituted benzene and unreacted disubstituted benzene substantially as a liquid or a solid-liquid slurry, and such that the concentration of residual molecular oxygen in the gas removed from the second oxidation stage is in the range of from about 3 to about 16 volume percent; (f) recovering from the second oxidation stage the second product mixture comprising the acid derivative product, and (g) withdrawing from the second oxidation stage and recycling to the first oxidation stage the residual molecular oxygen-containing gas.

The present invention is also the solution or solid-liquid slurry produced in step (b).

BRIEF DESCRIPTION OF THE FIGURES

For a more complete understanding of this invention, reference should now be made to the embodiment illustrated in greater detail in the accompanying drawings and described below by way of examples of the invention. In the drawings.

It should be understood that FIG. 1 is schematic in nature. In certain instances, details which are not necessary for an understanding of the present invention or which render other details difficult to perceive may be omitted. It should be understood, of course, that the invention is not necessarily limited to the particular embodiments illustrated herein.

DETAILED DESCRIPTION OF THE PREFERRED EMBODIMENTS

Feed mixture components for the process of this invention include at least one aromatic hydrocarbon having at least one oxidizable substituent group capable of being oxidized to a corresponding dicarboxylic acid, that is, the acid derivative product. Preferred feed mixture components include at least one disubstituted benzene material having any of a variety of substituents selected from the class consisting of alkyl, hydroxyalkyl, aldehyde, and carboxyalkyl groups, together with mixtures of these. Particularly preferred feed mixture components include the paradisubstituted benzene derivatives having alkyl groups as substituents, the acid derivative of which is terephthalic acid, and the partially oxidized forms thereof include mono- and di-alcohols and -aldehydes thereof, and the monoacid thereof, such as p-hydroxymethyl benzoic acid, p-tolualdehyde, and p-toluic acid. The alkyl groups preferably contain 1-4 carbon atoms, and are most preferably methyl groups. Accordingly, an especially preferred feed mixture component is paraxylene.

The at least one disubstituted benzene employed in the present invention is provided in a solution with the solvent preferably being an organic acid solvent. Preferably organic acids include organic acids having from one to six carbon atoms plus one carboxyl group, such as benzoic acid. The most preferred solvent is acetic acid due to its vapor pressure at preferred reactor temperatures, and its solvent capabilities. These organic acids are solvents for reasonable concentrations of the feed components, the catalyst system components, the intermediate oxidation products and the dicarboxylic acid product. The disubstituted benzene feed is preferably provided in a solution of between about 5 and about 25 weight percent.

The feed mixture components also comprise at least one catalytic metal selected from the class consisting of manganese, cobalt, nickel, zirconium, hafnium, cerium and mixtures thereof, and a bromine-affording material. Preferably the catalytic metals are cobalt and manganese. The catalytic metals may be in any form that is soluble in the reaction medium. Examples of such soluble forms include organic acid salts, basic salts, complex compounds and alcoholates. The catalytic metal component can be added to the reaction mixture with the disubstituted benzene or separately. Other metals and promoters may also be present in the catalyst system employed in the present invention. The bromine-affording material can be molecular bromine, a bromide or bromate salt, hydrobromic acid, a bromine-substituted organic compound, or a mixture of any or all of these.

The oxidant employed in the present invention is oxygen, which for the purpose of this invention means molecular oxygen. The source of the oxygen employed in this invention is typically pure oxygen, air or enhanced air containing additional amounts of oxygen.

From about 7, preferably from about 15, to about 60, preferably to about 35, weight percent of the total amount of disubstituted benzene to be added in steps (a) and (d) is added in the first oxidation stage (a). The Comparative Example A hereinafter illustrates that if all of the p-xylene to be introduced in steps (a) and (d) is introduced in step (a), then the optical density (1.79) of the resulting terephthalic acid product is unacceptably high. Optical density at 340 nm (OD 340) measures the concentration of undesirable high molecular-weight compounds that cause yellowness and fluorescence. Preferably from about 20, more preferably from about 40, to about 100, weight percent of the aforesaid predetermined total amount to be added in steps (a) and (d) of each of the catalytic metals, preferably cobalt and manganese, is added in the first oxidation stage. Preferably from about 20, more preferably from about 40, to about 100, weight percent of the aforesaid predetermined total amount to be added in steps (a) and (d) of bromine is added in the first oxidation stage. Preferably from about 10, more preferably from about 40, preferably to about 100, weight percent of the total amount of solvent to be added in steps (a) and (d) is added in the first oxidation stage.

In respect to the first oxidation stage alone, the mole ratio of bromine-to-total catalytic metals is from about 1:20, preferably from about 1:5, more preferably from about 1:4, to about 5:1, preferably to about 2:1, more preferably to about 1:1. The weight ratio of catalytic metals-to-solvent in the first oxidation stage is from about 150, preferably from about 400, to about 10,000, preferably to about 5,000, parts by weight of catalytic metals per million parts of solvent. The atom ratio of manganese-to-cobalt in the first oxidation stage is in the range of from about 1:100, preferably from about 1:5, to is about 100:1, preferably to about 5:1.

The reaction temperature in the first oxidation stage is in the range of from about 250° F., preferably from about 277° F., to about 401° F., preferably to about 351° F. The reaction pressure in the first oxidation stage is sufficiently high at the temperature employed to maintain the solvent, partially oxidized disubstituted benzene, acid derivative product and unreacted disubstituted benzene therein substantially as a liquid or solid-liquid slurry. Typically, the reaction pressure in the first oxidation stage is in the range of from about 130 to about 215 psig.

The concentration of oxygen in the oxygen-containing gas introduced into the first oxidation stage is in the range of from about 3, preferably from about 4, to about 20, preferably to about 11, more preferably to about 8, volume percent of oxygen. The reaction conditions are selected such that the concentration of residual oxygen in the gas removed from the first oxidation stage is from about 0.3 to about 2, preferably to about 1, volume percent. Under such conditions, from about 25, preferably from about 60, more preferably from about 70 to about 99.95 weight percent of the disubstituted benzene fed to the first oxidation stage is partially or completely oxidized in the first oxidation stage., Comparative Examples A and B illustrate that when the oxygen content of the vent gas from the first oxidation stage is less than 0.3%, then the optical density (1.79 and 1.08) of the resulting terephthalic acid product is unacceptably high.

In respect to the second oxidation stage alone, the mole ratio of bromine-to-total catalytic metals is from about 1:20, preferably from about 1:5, more preferably from about 1:4, to about 5:1, preferably to about 2:1, more preferably to about 1:1. The weight ratio of catalytic metals-to-solvent in the second oxidation stage is from about 150, preferably from about 400, to about 10,000, preferably to about 5,000 parts by weight of catalytic metals per million parts of solvent. The atom ratio of manganese-to-cobalt in the second oxidation stage is in the range of from about 1:100, preferably from about 1:5, to about 100:1, preferably to about 5:1.

The reaction temperature in the second oxidation stage is in the range of from about 347° F., preferably from about 360° F., to about 421° F., preferably to about 401° F. The reaction pressure in the second oxidation stage is sufficiently high at the temperature employed to maintain the solvent, acid derivative product, partially oxidized disubstituted benzene and unreacted disubstituted benzene substantially as a liquid or solid-liquid slurry. Typically, the reaction pressure in the second oxidation stage is in the range of from about 170 to about 235 psig. The temperature in the first oxidation stage is preferably at least 5.5° F., more preferably at least 40° F., lower than the temperature in the second oxidation stage. The pressure in the first oxidation stage is at least 5, more preferably at least 20 psig lower than the pressure in the second oxidation stage.

The concentration of oxygen in the oxygen-containing gas introduced into the second oxidation stage is in the range of from about 15, preferably from about 20, to about 50, preferably to about 25, volume percent of oxygen. The reaction conditions are selected within the above ranges therefor such that the concentration of residual oxygen in the gas removed from the second oxidation stage is from about 3, preferably from about 4, to about 15, preferably to about 11, more preferably to about 8 volume percent. Under such conditions, from about 97, preferably from about 99 weight percent, to about 100 weight percent of the disubstituted benzene and partially oxidized disubstituted benzene fed to the second oxidation stage is oxidized in the second oxidation stage.

The first oxidation stage can be comprised of a single reactor or of a plurality of reactors operated in parallel. Similarly, the second oxidation stage can be comprised of a single reactor or of a plurality of reactors operated in parallel. Thus, a first oxidation stage comprising a plurality of reactors, for example, four reactors, can be used with a second oxidation stage comprising a single reactor. In that case, the slurry or solution product from all of the reactors in the first oxidation stage could be fed to the single reactor in the second oxidation stage, and the oxygen in the vent gas from the single reactor in the second oxidation stage could be recycled to and split between the four reactors in the first oxidation stage. In an alternative, a first oxidation stage comprising a single reactor could be used with a second oxidation stage comprising a plurality of reactors, for example, four reactors. In that case, the slurry or solution product from the single reactor in the first oxidation stage could be split and fed to each of the four reactors in the second oxidation stage.

Figure 1:
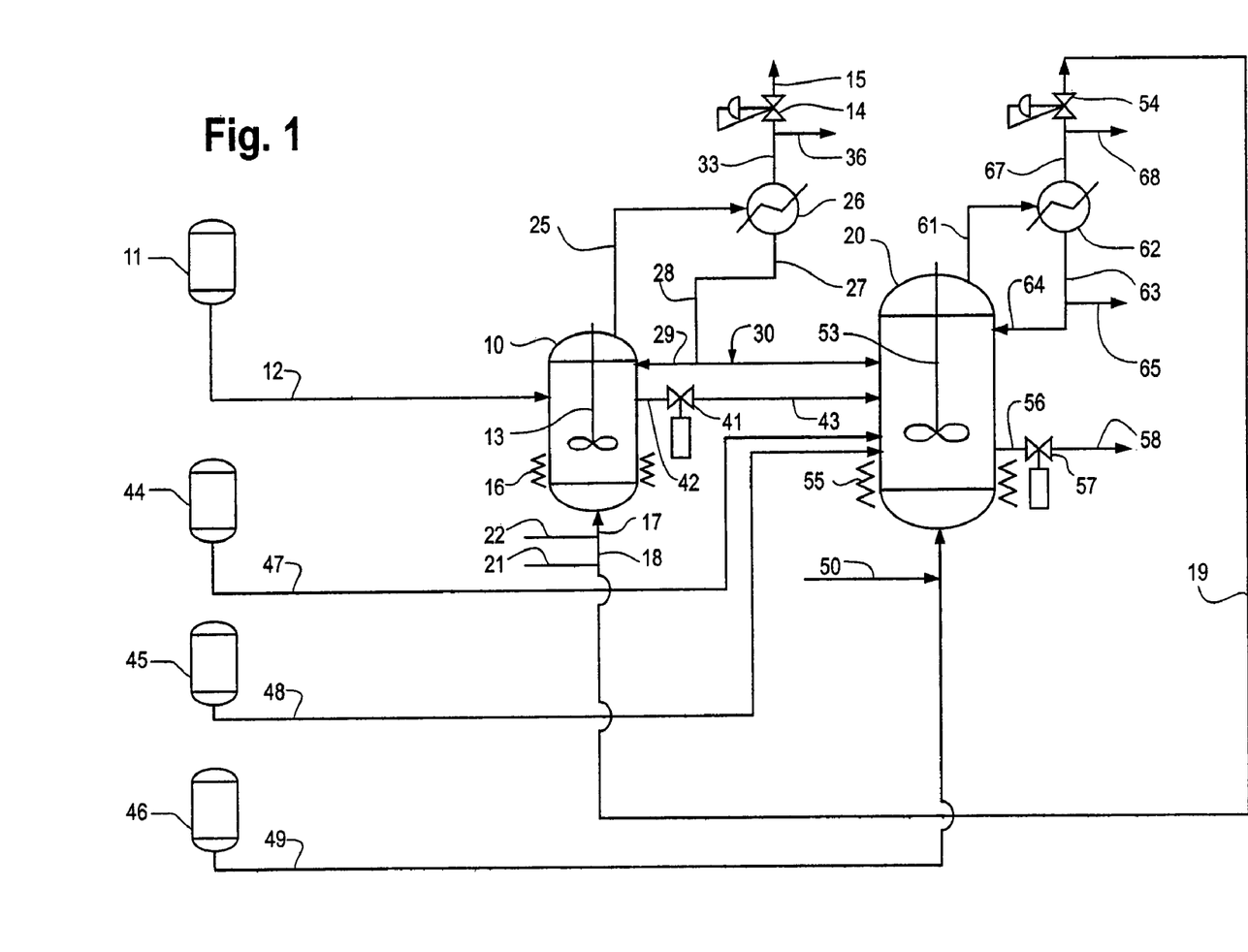
FIG. 1 is a schematic illustration of one embodiment of the method of this invention employing stagewise continuous countercurrent oxidation of paraxylene that affords the production of high quality terephthalic acid with maximum utilization of oxygen.

One embodiment of the method of this invention on which Illustrative Examples 1-18 and Comparative Examples A and B are modeled is illustrated by the schematic drawing in FIG. 1. For the purpose of this illustration, the disubstituted benzene employed is paraxylene, its acid derivative is terephthalic acid, and its partially oxidized disubstituted benzenes (oxidation intermediates) include para-hydroxymethyl benzoic acid, p-tolualdehyde, 4-carboyxbenzaldehyde and p-toluic add. A solution of paraxylene and the above described catalyst components in an acetic acid solvent is introduced into a first reactor 10 from a feed tank 11 through line 12. The contents of the first reactor 10 are kept well mixed using an agitator 13, and the reactor pressure is maintained at the desired level with a pressure regulator 14 in vent line 15 from the first reactor 10. The temperature of the contents of the first reactor 10 is regulated using a heater wrapping 16 around the first reactor 10. Oxygen is introduced into the first reactor 10 through lines 17 and 18 in a vent gas stream from the second reactor 20. If desired, additional oxygen as compressed air in line 21 can be combined with the vent gas stream from the second reactor 20 in order to increase the oxygen concentration in the gas stream entering the first reactor 10 through the lines 17 and 18. In the alternative, if desired, additional nitrogen can be combined through the line 22 with the vent gas stream from the second reactor 20 in order to reduce the oxygen concentration in the gas stream entering the first reactor 10 through the line 17.

The paraxylene and oxygen react in the first reactor 10 to form a product solution or slurry containing unreacted paraxylene, oxidation intermediates thereof and terephthalic acid. The exothermic heat of reaction is removed by vaporization of some of the solvent. An off-gas stream comprising the vaporized solvent, nitrogen (from the air) and unreacted oxygen is withdrawn from the first reactor 10 through line 25 to a condenser 26 where most of the vaporized solvent Is condensed and either returned to the first reactor 10 through lines 27, 28 and 29, or passed to the second reactor 20 through lines 27, 28 and 30 or split with a first portion being returned to the first reactor 10 through the lines 27, 28 and 29, and a second portion being passed to the second reactor 20 through the lines 27, 28 and 30. The noncondensable vapor is withdrawn through line 33 and the vent line 15 while a slipstream of the non-condensable vapor is withdrawn for analysis through the line 36 in order to monitor the extent of reaction and is concentration of unreacted oxygen in the vent gas.

The level of the product solution or slurry in the first reactor 10 is maintained by a valve 41 between the first reactor 10 and the second reactor 20. The pressure in the first reactor 10 can be maintained higher than the pressure in the second reactor 20 so that when the valve 41 is open, product solution or slurry is transferred from the first reactor, to the second reactor 20 through lines 42 and 43. In the alternative, a pump (not shown) in line 42 or 43 can be used to pump the solution or slurry from the first reactor 10 to the second reactor 20. If necessary or desired, additional amounts of one or more of paraxylene, one or more of the catalyst components, solvent and/or bromine can be introduced to the second reactor 20 from tanks 44, 45 and 46, respectively, through the lines 47, 48 and 49, respectively. Compressed air is introduced through line 50 into the second reactor 20.

When the disubstituted benzene being oxidized is p-xylene, the composition of the product from the first oxidation stage on a solvent-free basis as a percentage of the total product mixture comprises from about 5.0 to about 85.0 weight percent of the terephthalic acid, from about 2.0 to about 20.0 weight percent of 4-carboxybenzaldehyde, from about 0.0 to about 3.0 weight percent of hydroxymethylbenzoic acid, from about 5.0 to about 65.0 weight percent of p-toluic acid, from about 0.0 to about 30.0 weight percent of p-tolualdehyde, and from about 0.0 to about 35.0 weight percent of p-xylene.

As with the first reactor 10, the contents of the second reactor 20 are kept well mixed using an agitator 53, and the reactor pressure is maintained at the desired level with a pressure regulator 54 in vent line 19 from the second reactor 20. The temperature of the contents of the second reactor 20 is regulated using a heater wrapping 55 around the second reactor 20. Oxygen reacts with the unreacted paraxylene and oxidation intermediates thereof in the second reactor 20 to form a product solution or slurry containing terephthalic acid. The oxidation of paraxylene and its oxidation intermediates to terephthalic acid is effected to a high degree of completion in the second reactor 20. The resulting product solution or slurry of terephthalic acid is then withdrawn from the second reactor 20 through line 56, slugging valve 57 and line 58.

Within the second reactor 20 the exothermic heat of reaction is removed by vaporization of some of the solvent. An off-gas stream comprising the vaporized solvent, nitrogen and unreacted oxygen is withdrawn from the second reactor 20 through line 61 to a condenser 62 where most of the vaporized solvent is condensed and returned to the second reactor in lines 63 and 64. A slipstream of the condensed solvent is withdrawn for analysis through line 65. The non-condensable vapor is withdrawn through lines 67 and 19 while a slipstream of non-condensable vapor is withdrawn for analysis through the line 68 in order to monitor the extent of reaction and the concentration of unreacted oxygen in the vent gas from the second reactor 20.

The resulting solution or slurry of the aromatic acid product withdrawn from the second oxidation reactor is then typically subjected to crystallization as described in the aforesaid U.S. Pat. No. 3,092,658 in column 2, lines 46-63; U.S. Pat. No. 2,962,361 in column 2, line 43 to column 3, line 2; and U.S. Pat. No. 3,064,044 in column 3, lines 47-71. In one embodiment, the solution or slurry of the aromatic acid withdrawn from the second oxidation reactor is passed to one or more vessels where it is contacted with air under oxidation conditions to further oxidize intermediate impurities. The solution or slurry is then subjected to crystallization, as described hereinabove. Typically, the aromatic acid can be recovered by centrifugation or filtration, and then purified issuing a hydrogenation catalyst and water solvent, as is well known in the art.

This invention is applicable to any aromatic acid purification process, such as those known in the art, examples of which are described in U.S. Pat. Nos. 5,354,898 and 5,362,908, both of which are incorporated by reference. In general, an aromatic acid purification process comprises the hydrogenation of dissolved crude aromatic acid within a purification liquid stream comprising solvent to produce dissolved purified aromatic acid. The dissolved purified aromatic acid is then crystallized and the resulting solid, purified acid separated, from the purification liquid stream, typically by filtration.

The invention may be suitably used in an aromatic acid purification process, wherein crude aromatic acid (e.g. crude terephthalic acid) is dissolved in a purification liquid stream comprising solvent and treated with hydrogen in a pressure reactor vessel in a first reaction zone containing a hydrogenation catalyst. The hydrogenation catalyst of the pressure reactor vessel typically comprises one or more active hydrogenation catalyst components supported on a carrier material.

The carrier material is typically in a granular form, although pellets or other types of particulate forms may be used. When in a granular form, the granules preferably have an average size of −2 mesh to −12 mesh (U.S. Sieve Series), more preferably −4 mesh to −8 mesh. The carrier material is preferably an active carbon, and is more preferably derived from coconut charcoal. Such active carbon typically has a surface area of at least 600 m2/gram (N2, BET Method), preferably 800 m2/gram to 1500 m2/gram. While active carbon derived from coconut charcoal in the form of granules is preferred as a support material for the hydrogenation catalyst component, other porous carbonaceous, metal oxide or other supports or substrates may be used.

The hydrogenation catalyst contains at least one active catalytic hydrogenation component. Particularly suitable catalytic hydrogenation components are the Group VIII metals of the Periodic Table of Elements (IUPAC version), including palladium, platinum, rhodium, osmium, ruthenium, iridium, and mixtures thereof. The catalytic hydrogenation catalyst component may be deposited on, or added to, the carbon or other carrier material by any suitable method, for example, by treating the carrier with a solution of one or more soluble Group VIII metal compounds, such as palladium chloride, and then drying the result to remove excess solvent.

A preferred loading of the Group VIII metal on the carrier is in the range of 0.01 to 2 wt % based on the total weight of the finished catalyst, i.e., the total weight being the weight of the dry carbon carrier and the active hydrogenation component. More preferably, the Group VIII metal loading on the carbon carrier is 0.2 to 0.8 wt %.

Suitable catalysts and catalyst beds useful in the embodiment of this invention relating to aromatic acid purification are described, for example, in U.S. Pat. Nos. 4,394,299; 4,629,715; 4,728,630 and 4,892,972. A suitable palladium-on-carbon catalyst may be obtained, for example, from Engelhard Corporation, Edison, N.J. Also, suitable rhodium-on-carbon catalysts may be obtained from Engelhard Corporation.

A suitable reactor for hydrogenation is any reactor vessel that can withstand the temperature and pressure used for the hydrogenation of a crude aromatic acid dissolved in purification solvent. The preferred reactor configuration is a cylindrical reactor positioned with its axis vertically disposed and having the hydrogenation catalyst contained therein in a fixed bed. In the preferred mode of operation, crude aromatic acid dissolved in a purification solvent is added to the reactor vessel at a position at or near the top portion of the reactor vessel, and the crude aromatic acid dissolved in the purification liquid stream flows down through the bed of hydrogenation catalyst contained in the reactor vessel in the presence of hydrogen gas, wherein impurities are reacted with hydrogen gas. In this preferred mode, the crude aromatic acid is purified and the purified product is removed from the reactor vessel at a position at or near the bottom of the reactor.

In a suitable reactor vessel apparatus, a hydrogenation catalyst preferably comprising a carbon carrier and an active hydrogenation catalyst component supported on the carrier is held within the reactor vessel by a screen or other means that retains the catalyst particles in the reactor, yet allows the relatively free passage of crude aromatic acid dissolved in the purification liquid stream. The means used for retaining the catalyst particles may be a flat mesh screen or a screen made by closely spaced parallel wires. Other suitable catalyst retaining means include, for example, a tubular Johnson screen or a perforated plate. The means used for retaining the catalyst particles is constructed of a material that is suitably resistant to corrosion and is of an appropriate strength to efficiently retain the catalyst bed. Most suitably, the means used for retaining the catalyst bed has openings of 1 mm or less and is constructed of a metal such as stainless steel, titanium or Hastelloy C.

The reactor may be operated in several modes. For example, a predetermined liquid level may be maintained in the reactor and hydrogen may be fed in, for any given reactor pressure, at a rate sufficient to maintain the predetermined liquid level. The difference between the actual reactor pressure and the vapor pressure of purification liquid stream present is the hydrogen partial pressure in the reactor vapor space. Alternatively, if hydrogen is fed in admixture with an inert gas such as nitrogen, the difference between the actual reactor pressure and the vapor pressure of the crude acid solution present is the combined partial pressure of hydrogen and the inert gas admixed therewith. In this case the hydrogen partial pressure may be calculated from the known relative amounts of hydrogen and inert gas present in the mixture. In yet another operating mode, the reactor may be filled with a purification liquid stream so as to provide no reactor vapor space. That is, the reactor may be operated as a hydraulically full system with dissolved hydrogen being fed to the reactor by flow control. In such an instance, the concentration of hydrogen in solution may be modulated by adjusting the hydrogen flow rate to the reactor. If desired, a pseudohydrogen partial pressure value may be calculated from the solution hydrogen concentration which, in turn, may be correlated with the hydrogen flow rate to the reactor.

In the operating mode where process control is effected by adjusting the hydrogen partial pressure, the hydrogen partial pressure in the reactor is preferably in the range of 10 pounds per square inch gauge to 200 pounds per square inch gauge (69-1379 kPa) or higher, depending upon the service pressure rating of the reactor, the degree of contamination of the aforementioned crude aromatic acid, the activity and age of the particular catalyst employed, and other processing considerations known to persons skilled in the art. In the operating mode where process control is effected by directly adjusting the hydrogen concentration in the feed solution, the latter usually is less than saturated with respect to hydrogen and the reactor itself is hydraulically full. Thus, an adjustment of the hydrogen flow rate to the reactor will result in the desired control of hydrogen concentration in the solution. In general, the amount of hydrogen to be supplied to the purification reactor under reaction conditions is, of course, sufficient to effect the desired hydrogenation.

The space velocity, reported as weight of the crude aromatic acid per weight of catalyst per hour, during hydrogenation is typically from 1 hour$^{-1}$ to 25 hour$^{-1}$, preferably from 2 hours$^{-1}$ to 15 hours$^{-1}$. The residence time of the purification liquid stream in the catalyst bed varies, depending upon the space velocity.

After hydrogenation, the hydrogenated stream, now comprising purified aromatic acid and solvent, is removed from the reactor and cooled to a crystallization temperature. The crystallization temperature is sufficiently low (e.g., 320° F. or below) for crystallization of the purified aromatic acid to occur, thereby producing crystals within the liquid phase. The crystallization temperature is sufficiently high so that impurities and their reduction products (products resulting from hydrogenation) remain dissolved in the liquid phase. Thereafter, the liquid, containing dissolved impurities and their reduction products, is separated (typically by centrifugation or filtration) from the crystallized purified aromatic acid.

A particularly desirable application of the method of the present invention is in conjunction with one or more existing oxidation reactor(s). In this case, the existing reactor(s) would serve as the second stage in the method of this invention and a pre-oxidation reactor would be installed and employed as the first stage in conjunction with the existing reactor(s) as the second stage. The result would be an effective increase in the production capacity of the existing reactor(s) without the use of additional air or compressor capacity and without any significant reduction in the quality or yield of the acid derivative produced or additional solvent usage.

The present invention will be more clearly understood from the following examples, which are illustrative, without limitation, of the improved oxidation process of this invention.

Illustrative Examples 1-18 and Comparative Examples A and B

The feed solution in each of Illustrative Examples 1-18 and Comparative Examples A and B was made up of measured amounts of solvent (acetic acid and water), catalyst (cobalt acetate, manganese acetate and hydromide) and paraxylene (PX), and was stored in a solvent/catalyst/PX feed tank. This feed was pumped into the first reactor at a fixed rate. Amounts of nitrogen and compressed air were mixed to produce a stream that is equal to the volume and had the same oxygen content of the, stream of non-condensable vapor that was withdrawn from the second reactor. Thus the resulting stream of compressed air and nitrogen being fed to the first reactor simulated the composition and volume of the vent stream from the second reactor and was introduced to the first reactor.

The first reactor contents were kept well mixed with an agitator. The reactor pressure was maintained at the desired level with a pressure regulator in a vent line for venting non-compressed vent gas from the first reactor. The reactor temperature was regulated with a heater wrapping around the reactor. The reactor level was maintained by opening and closing a valve between the first and the second reactor. For experimental convenience, the first reactor pressure was maintained slightly higher than the second reactor pressure so that material was transferred by differential pressure from the first reactor to the second reactor when that valve was open.

The PX and the oxygen reacted in the first reactor to form a reaction solution or slurry containing unreacted PX, oxidation intermediates thereof and terephthalic acid as the final oxidation product. The heat of reaction was removed by vaporizing some of the solvent. The vent stream from the first reactor was sent to a condenser where most of the solvent vapor was condensed. The condensed reflux was either returned to the first reactor or passed to the second reactor or a combination of both. A slip stream of the non-condensable vapor was withdrawn and analyzed to monitor the extent of the reaction.

The reaction solution or slurry was passed from the first reactor to the second reactor. Additional solvent and PX were also fed at specified rates to the second reactor. The amount of compressed air added to the second reactor was such that the oxygen concentration in the vent from this reactor was at the desired level. The control of the second reactor was similar to that of the first reactor, except that a small slip stream was removed from the reflux to control the water concentration of the reactor content at the desired level. The oxidation of the PX and its oxidation intermediates in the second reactor were carried to a high degree of completion. The terephthalic acid product was removed from the second reactor through a slugging valve.

The specific reaction conditions employed and results for Illustrative Examples 1-18 and Comparative Examples A and B are presented in Tables 1-7. In Tables 1-7, PX, HAc, HMBA, TA, 4CBA and BA represent p-xylene, acetic acid, hydroxymethylbenzoic acid, terephthalic acid, 4-carboxybenzaldehyde and benzoic acid, respectively. H2O conc in the last column of Table 1 under Reactor Liquid represents the concentration of water in the first reactor that includes the water formed in the oxidation reaction.

SCFH means standard cubic feet per hour. HAc burn means the amount of acetic is acid consumed in the example and is reported as pounds of HAc per thousand pounds of PX (lbs/M1bPX). The solvent ratio in Table 4 is reported as pounds of solvent per pound of the total PX feed to both reactors (lb solv./lb total PX feed). OD 340 represents the optical density of TA at 340 nm after it has been recovered, washed and filtered.

Comparative Examples 1-9

The same procedure employed for Examples 1-18 was also employed for Comparative Examples 1-9, except that Comparative Examples 1-9 did not employ two oxidation reactors. A single oxidation reactor was employed and was controlled in substantially the same manner as the second oxidation reactor employed in Examples 1-18. All of the components of the reaction mixture were introduced directly into the single oxidation reactor employed. The non-condensable vapor from the oxidation reactor was withdrawn from the reactor as described for the first oxidation reactor in Examples 1-18.

The specific reaction conditions employed and the results for Comparative Examples 1-9 are presented in Tables 8-11. The abbreviations and units employed in Tables 8-11 are the same as those employed in Tables 1-7. Comparison of the results of Comparative Examples 4, 5, 6 and 7 with that of Comparative Examples 1, 2, 3 and 8 illustrates that if the vent oxygen is lowered to about 1 volume percent from the normal of about 4 volume percent, the color of the terephthalic acid product, as measured by the optical density (OD 340), will increase significantly and render the TA product unacceptable.

Examples 1 through 18 illustrate that if the reduction of the vent oxygen to about 1 volume percent is achieved with staged countercurrent oxidation, the terephthalic acid product color as well as the amount of acetic acid burned is comparable to that of the current oxidation method, that is, about 4 volume percent vent oxygen without staged countercurrent oxidation. Comparison of the results of Examples 18 and 14 illustrates that the amount of disubstituted benzene introduced in the first reactor can range from 20 to 55 weight percent of the predetermined total amount of disubstituted benzene introduced in both reactors. Examples 1 through 18 illustrate that the feed gas to the first reactor can contain 4 to 6 volume percent of oxygen. Examples 1 and 18 Illustrate that the temperature of the first reactor can range from 277° F. to 321° F. Examples 8 and 17 illustrate that about 79 to 99.3 weight percent of the disubstituted benzene fed to the first oxidation stage is oxidized. Examples 13 and 14 illustrate that the concentration of residual molecular oxygen in the remaining gas mixture from the first reactor can range from 0.73 to 1.66 volume percent.

Figure 2:
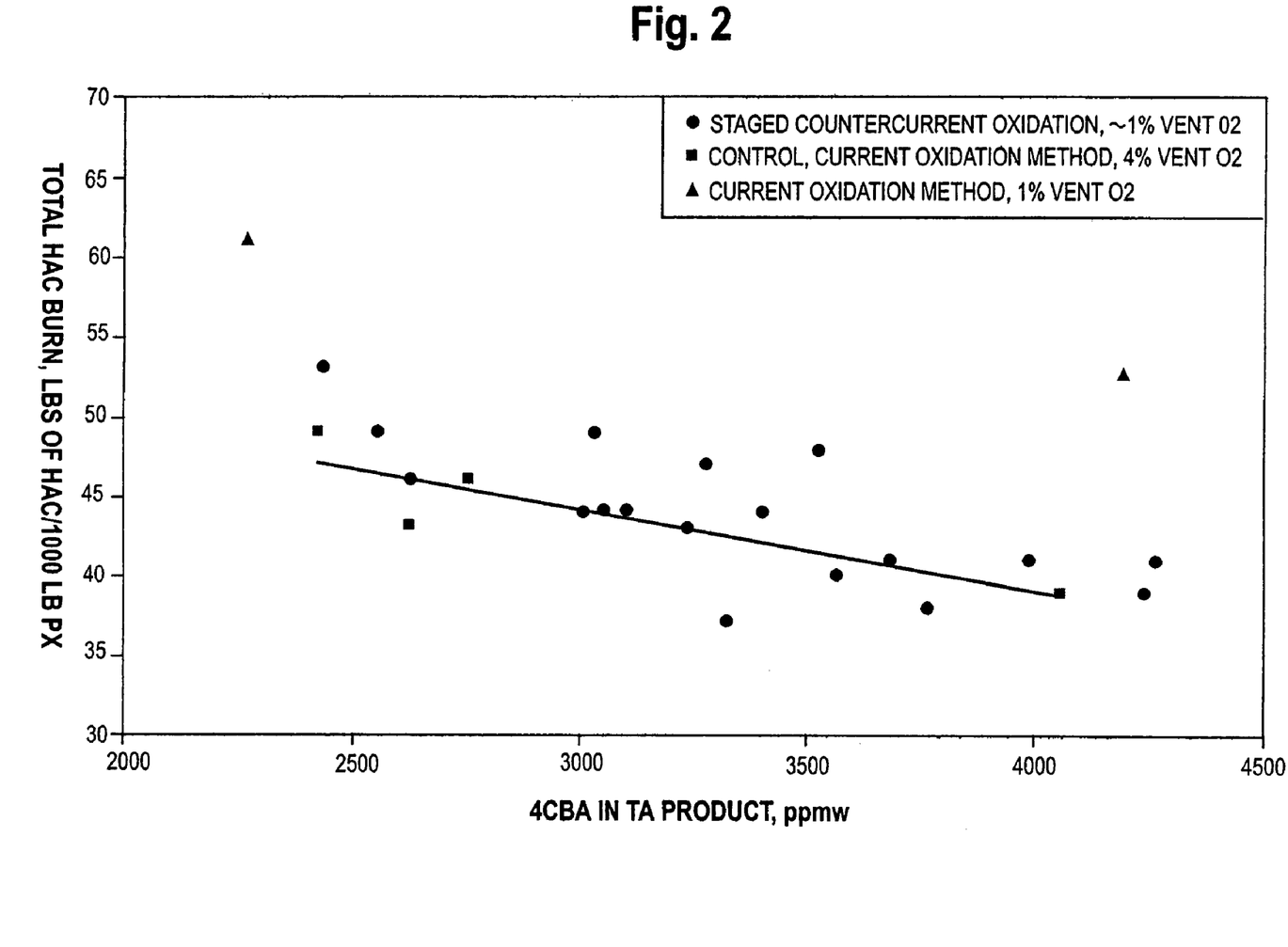
FIG. 2 contains a series of plots of the total acetic acid burn versus the concentration of 4-carboxybenzaldehyde in the reactor for a number of the illustrative examples and comparative examples hereinbelow.
Figure 3:
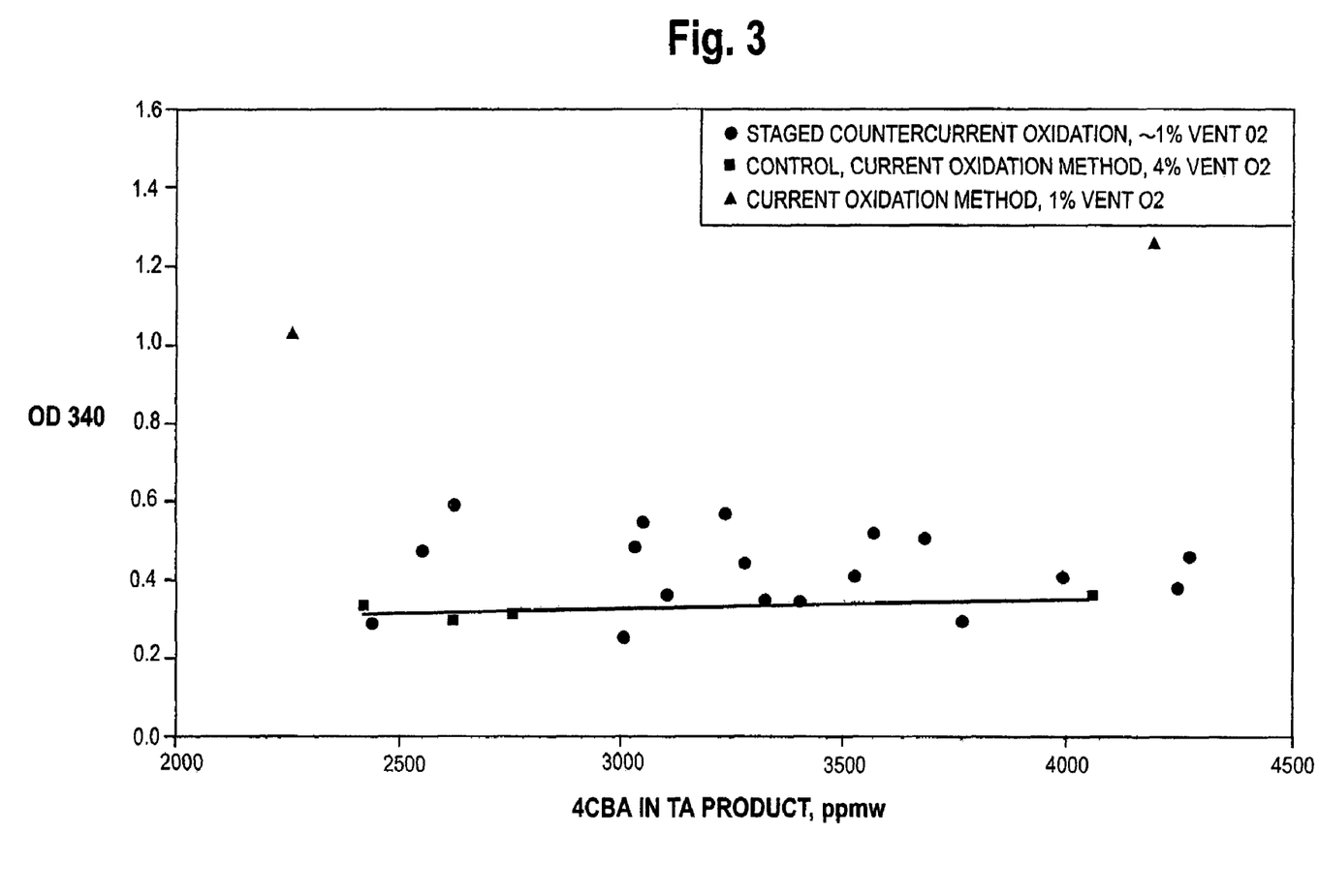
FIG. 3 contains a series of plots of the optical density of the terephthalic acid product after it has been recovered, washed and dried versus the concentration of 4-carboxybenzaldehyde in the reactor for a number of the illustrative examples and comparative examples hereinbelow.

FIGS. 2 and 3 contain plots that illustrate the effect of the concentration of 4-carboxybenzaldehyde (4-CBA) in the oxidation reactor on (a) the total acetic acid burn (measured in lbs of acetic acid per 1000 lbs of paraxylene) and (b) the optical density at 340 nm of the terephthalic acid product after it had been recovered, washed and dried. The plots in FIG. 2 illustrate that the total acetic acid burn for runs with staged countercurrent oxidation are comparable to those for runs without staged countercurrent oxidation with 4 volume percent vent oxygen, when the results are compared on the basis of equal 4-CBA weight percent in the terephthalic acid product. It further illustrates that if the vent oxygen is lowered to 1 volume percent without staged countercurrent oxidation, the resulting acetic acid burn is much higher. Similarly, the plots in FIG. 3 illustrate that the optical density for runs with staged countercurrent oxidation is comparable to those for runs without staged countercurrent oxidation with 4 volume percent vent oxygen. It further illustrates that if the vent oxygen is lowered to 1 volume percent without staged countercurrent oxidation, the optical density of the resulting terephthalic acid product is much higher. Thus, the plots in FIGS. 2 and 3 illustrate that the method of the present invention affords an economic method of operation while providing an acid derivative product of a quality that is comparable to or not unacceptabably different from similar products that are commercially manufactured and marketed today.

For practical implementation of the method of the present invention, the highest allowable temperature, for example 300° F., for the first oxidation reactor may be limited by the overall process configuration, in particular, the pressure of the second reactor and the heat balance. Once the temperature limit is set, one or more other variables must be adjusted to achieve a vent oxygen that is less than or equal to about 2%. Examples include the following: paraxylene in the feed, amount of catalyst added, residence time, and increased catalyst concentration in the reactor achieved by reducing the amount of solvent added. In this regard, it is shown in Examples 8 and 9 that where the ratio of oxygen to paraxylene (ox/PX) in the first reactor is too low (that is, too much parxylene in the feed because the amount of oxygen is fixed by the volume fed to it from the second reactor and the volume desired to be vented from the first reactor), that the result is less desirable because a significant amount of paraxylene is unreacted and the color of the terephthalic acid product is increased (0.58 and 0.56, respectively). Similarly, since all of the effluent from the first reactor is passed directly to the second reactor, all of the catalyst added to the first reactor ends up in the second reactor as well. Consequently, the amount of catalyst that can be added is determined by the requirements for catalyst in the second reactor also and thus is not really a completely independent variable for the first reactor. Furthermore, for the same throughput, longer residence time can be achieved by larger reactor volume, but that may not be desirable because it increases cost. In addition, after the second reactor, most of the solvent is separated from the product and is recycled. This recycled solvent stream (mother liquor) also contains most of the recycled catalyst. The amount of catalyst free solvent that must be added to the reactor stages is not large. Consequently, it is impossible to reduce the amount of solvent added to the first reactor very much, without also reducing the catalyst at the same time.

By contrast, a very convenient way to increase the catalyst concentration and the residence time in the first reactor at the same time is to send all or some of the condensed reflux from the first reactor to the second reactor, bypassing the first reactor. As a result, the amount of solvent in the first reactor effluent is reduced, thus increasing the catalyst concentration and the residence time in the first reactor. Examples 2 and 6 indicate that this approach is successful in lowering the oxidation temperature (287° F. and 279° F., respectively in the first reactor), and still achieve only about 1 volume percent of oxygen in the vent gas from the first reactor. The product

TABLE 1

First Reactor Conditions

| | Feed Composition | | | | | Reactor Liquid | | | |
|---|---|---|---|---|---|---|---|---|---|
| | (wt. Fraction) | | | Liquid | PX feed | | | | H2O |
| Example No. | PX conc. | HAc conc | H2O conc | feed rate (lb/hr) | rate (lb/hr) | Co conc (ppmw) | Mn conc (ppmw) | Br conc (ppmw) | conc. (wt. %) |
| 1 | 0.089 | 0.871 | 0.035 | 7.4 | 0.66 | 490 | 450 | 670 | 5.3 |
| 2 | 0.070 | 0.861 | 0.064 | 7.2 | 0.50 | 960 | 890 | 1420 | 6.2 |
| 3 | 0.064 | 0.897 | 0.034 | 7.8 | 0.50 | 970 | 900 | 1400 | 3.9 |
| 4 | 0.082 | 0.880 | 0.034 | 8.1 | 0.66 | 500 | 470 | 700 | 6.0 |
| 5 | 0.089 | 0.871 | 0.035 | 7.4 | 0.66 | 460 | 430 | 640 | 5.9 |
| 6 | 0.063 | 0.897 | 0.034 | 7.8 | 0.49 | 900 | 840 | 1190 | 5.1 |
| 7 | 0.082 | 0.880 | 0.034 | 8.0 | 0.66 | 470 | 450 | 640 | 5.5 |
| 8 | 0.099 | 0.832 | 0.066 | 11.1 | 1.10 | 340 | 310 | 490 | 8.1 |
| 9 | 0.099 | 0.832 | 0.066 | 11.1 | 1.10 | 330 | 330 | 450 | 7.8 |
| 10 | 0.062 | 0.866 | 0.068 | 10.6 | 0.66 | 380 | 360 | 520 | 9.1 |
| 11 | 0.094 | 0.837 | 0.066 | 11.1 | 1.04 | 370 | 360 | 540 | 8.5 |
| 12 | 0.062 | 0.867 | 0.068 | 10.6 | 0.66 | 360 | 340 | 470 | 9.1 |
| 13 | 0.061 | 0.868 | 0.067 | 10.7 | 0.65 | 360 | 340 | 500 | 8.4 |
| 14 | 0.145 | 0.790 | 0.062 | 11.7 | 1.70 | 310 | 310 | 440 | 8.1 |
| 15 | 0.092 | 0.838 | 0.066 | 11.0 | 1.01 | 430 | 410 | 590 | 8.8 |
| 16 | 0.088 | 0.844 | 0.063 | 7.3 | 0.64 | 800 | 760 | 1220 | 6.9 |
| 17 | 0.077 | 0.854 | 0.064 | 7.2 | 0.55 | 870 | 810 | 1330 | 7.0 |
| 18 | 0.066 | 0.882 | 0.048 | 9.7 | 0.64 | 400 | 370 | 620 | 6.9 |
| A | 0.237 | 0.704 | 0.055 | 13.2 | 3.13 | 320 | 300 | 450 | 7.3 |
| B | 0.099 | 0.831 | 0.066 | 11.1 | 1.10 | 420 | 400 | 580 | 8.5 |

| | Gas feed rate (SCFH) | Feed gas Ox conc. (vol %) | Liquid Temp (° F.) | Pres (psig) | Residence time (min) |
|---|---|---|---|---|---|
| 1 | 139 | 4.0 | 277 | 224 | 65 |
| 2 | 139 | 4.0 | 279 | 224 | 105 |
| 3 | 139 | 4.0 | 285 | 228 | 102 |

TABLE 1-continued

First Reactor Conditions

| | | | | | | |
|---|---|---|---|---|---|---|
| 4 | 139 | 4.0 | 286 | 228 | 54 |
| 5 | 139 | 4.0 | 286 | 224 | 55 |
| 6 | 139 | 4.0 | 287 | 230 | 105 |
| 7 | 139 | 4.0 | 289 | 228 | 53 |
| 8 | 139 | 4.0 | 296 | 226 | 40 |
| 9 | 139 | 4.0 | 296 | 228 | 40 |
| 10 | 139 | 4.0 | 307 | 230 | NA |
| 11 | 140 | 5.0 | 309 | 236 | 38 |
| 12 | 139 | 4.0 | 310 | 228 | NA |
| 13 | 139 | 4.0 | 319 | 226 | 39 |
| 14 | 142 | 6.0 | 320 | 238 | 38 |
| 15 | 142 | 6.0 | 320 | 236 | 37 |
| 16 | 141 | 5.0 | 300 | 220 | 85 |
| 17 | 141 | 5.0 | 320 | 232 | 101 |
| 18 | 141 | 5.0 | 321 | 226 | 47 |
| A | 141 | 5.0 | 310 | 240 | 34 |
| B | 139 | 4.0 | 312 | 224 | 39 |

TABLE 2

First Reactor Vent Gas Analysis

| Example No. | $O_2$ (mole %) | CO (mole %) | $CO_2$ (mole %) | HAc burn (lbs/Mlb PX) |
|---|---|---|---|---|
| 1 | 1.29 | 0.020 | 0.061 | 2.1 |
| 2 | 1.04 | 0.020 | 0.063 | 2.0 |
| 3 | 1.04 | 0.020 | 0.064 | 2.1 |
| 4 | 0.99 | 0.020 | 0.089 | 2.8 |
| 5 | 1.12 | 0.020 | 0.060 | 2.1 |
| 6 | 0.98 | 0.022 | 0.072 | 2.3 |
| 7 | 1.07 | 0.030 | 0.077 | 2.7 |
| 8 | 1.18 | 0.021 | 0.094 | 2.9 |
| 9 | 1.05 | 0.020 | 0.101 | 3.0 |
| 10 | 1.05 | 0.020 | 0.100 | 3.2 |
| 11 | 1.26 | 0.030 | 0.111 | 3.7 |
| 12 | 1.09 | 0.020 | 0.100 | 3.2 |
| 13 | 0.73 | 0.030 | 0.103 | 3.5 |
| 14 | 1.66 | 0.031 | 0.172 | 5.3 |
| 15 | 1.48 | 0.031 | 0.136 | 4.4 |
| 16 | 0.97 | 0.036 | 0.110 | 3.7 |
| 17 | 1.23 | 0.050 | 0.141 | 5.0 |
| 18 | 1.24 | 0.040 | 0.110 | 4.0 |
| A | 0.02 | 0.160 | 0.060 | 5.4 |
| B | 0.04 | 0.123 | 0.050 | 4.3 |

TABLE 3

First Reactor Slurry Analysis

| Example No. | PX (ppmw) | HMBA (wt %) | TA (wt %) | 4CBA (wt %) | BA (wt %) | p-Toluic Acid (wt %) | p-Tolualdehyde (wt %) |
|---|---|---|---|---|---|---|---|
| 1 | 7932 | 0.0630 | 2.5547 | 1.1090 | 0.0072 | 4.6928 | 1.1032 |
| 2 | 1690 | 0.0359 | 10.4327 | 1.1259 | 0.0131 | 1.9924 | 0.2860 |
| 3 | 1672 | 0.0450 | 9.8184 | 1.1259 | 0.0179 | 2.1545 | 0.2754 |
| 4 | 3923 | 0.0451 | 3.7772 | 1.0985 | 0.0115 | 4.0320 | 0.7933 |
| 5 | 6287 | 0.0614 | 3.5805 | 1.1647 | 0.0140 | 4.4613 | 0.9209 |
| 6 | 2045 | 0.0389 | 10.2378 | 1.0366 | 0.0164 | 1.9841 | 0.2431 |
| 7 | 5351 | 0.0538 | 3.5867 | 1.0560 | 0.0109 | 3.9052 | 0.8011 |
| 8 | 20400 | 0.0717 | 1.2950 | 0.7654 | 0.0062 | 5.8155 | 0.0437 |
| 9 | 20200 | 0.0590 | 1.0669 | 0.5970 | 0.0067 | 4.6045 | 1.7016 |
| 10 | 1227 | 0.0422 | 3.6372 | 0.8980 | 0.0110 | 3.2352 | 0.5270 |
| 11 | 9701 | 0.0691 | 2.7834 | 0.9799 | 0.0129 | 4.6190 | 1.0770 |
| 12 | 2751 | 0.0398 | 3.3118 | 0.8041 | 0.0131 | 3.0432 | 0.6055 |
| 13 | 2936 | 0.0431 | 3.7832 | 0.7352 | 0.0123 | 2.4505 | 0.4353 |
| 14 | 25100 | 0.1123 | 2.2876 | 0.9283 | 0.0200 | 7.5448 | 1.9578 |
| 15 | 4122 | 0.0579 | 6.2122 | 1.1759 | 0.0202 | 3.8555 | 0.6513 |
| 16 | 1105 | 0.0443 | 15.2025 | 0.9820 | 0.0201 | 1.5925 | 0.1996 |
| 17 | 561 | 0.0166 | 7.3153 | 0.1772 | 0.0113 | 0.2582 | 0.0296 |
| 18 | 1534 | 0.0252 | 6.4018 | 0.6594 | 0.0155 | 1.7461 | 0.2452 |
| A | 94500 | 0.1190 | 0.6753 | 0.4767 | 0.0111 | 7.1922 | 3.2307 |
| B | 10600 | 0.0814 | 2.4210 | 1.0217 | 0.0087 | 4.8588 | 0.0242 |

TABLE 4

Second Reactor Conditions

| | | Reactor Liquid | | | |
|---|---|---|---|---|---|
| Example No. | PX Feed Rate (lb/hr) | Solvent ratio (lb solv/lb total PX feed to both reactors) | Co conc. (ppmw) | Mn conc. (ppmw) | Br conc. (ppmw) |
| 1 | 2.4 | 2.86 | 390 | 360 | 520 |
| 2 | 2.6 | 2.87 | 400 | 370 | 560 |
| 3 | 2.6 | 3.01 | 374 | 341 | 520 |
| 4 | 2.4 | 2.98 | 410 | 380 | 500 |
| 5 | 2.4 | 2.54 | 370 | 320 | 470 |
| 6 | 2.6 | 3.06 | 380 | 360 | 500 |
| 7 | 2.4 | 3.01 | 360 | 340 | 450 |
| 8 | 2.0 | 2.58 | 420 | 410 | 550 |
| 9 | 2.0 | 2.92 | 350 | 350 | 460 |
| 10 | 2.4 | 3.24 | 390 | 360 | 490 |
| 11 | 2.1 | 3.02 | 400 | 410 | 540 |
| 12 | 2.4 | 3.07 | 360 | 340 | 470 |
| 13 | 2.4 | 2.82 | 390 | 350 | 510 |
| 14 | 1.4 | 3.06 | 360 | 350 | 470 |
| 15 | 2.1 | 2.93 | 460 | 450 | 590 |
| 16 | 2.5 | 2.79 | 390 | 370 | 550 |
| 17 | 2.5 | 2.74 | 390 | 360 | 580 |
| 18 | 2.5 | 2.49 | 410 | 400 | 610 |

TABLE 4-continued

Second Reactor Conditions

| | | | | | |
|---|---|---|---|---|---|
| A | 0.0 | 2.68 | 420 | 400 | 530 |
| B | 2.0 | 2.35 | 560 | 540 | 660 |

| Example No. | H2O conc (wt %) | Liquid Temp (° F.) | Pres (psig) | Air feed rate (SCFH) | Residence time (min) |
|---|---|---|---|---|---|
| 1 | 10.9 | 387 | 213 | 164 | 65 |
| 2 | 11.2 | 387 | 214 | 158 | 63 |
| 3 | 12.6 | 387 | 218 | 158 | 63 |
| 4 | 12.7 | 387 | 218 | 161 | 62 |
| 5 | 11.5 | 387 | 214 | 161 | 73 |
| 6 | 12.2 | 386 | 220 | 160 | 61 |
| 7 | 12.7 | 387 | 218 | 157 | 67 |
| 8 | 11.5 | 388 | 216 | 159 | 72 |
| 9 | 12.1 | 388 | 219 | 158 | 69 |
| 10 | 12.7 | 388 | 220 | 160 | 60 |
| 11 | 12.7 | 387 | 227 | 163 | 65 |
| 12 | 12.4 | 388 | 218 | 160 | 64 |
| 13 | 11.6 | 388 | 216 | 158 | 66 |
| 14 | 12.1 | 388 | 228 | 153 | 66 |
| 15 | 12.6 | 386 | 226 | 160 | 69 |
| 16 | 11.4 | 386 | 222 | 161 | 65 |
| 17 | 11.7 | 386 | 222 | 163 | 66 |
| 18 | 11.5 | 386 | 216 | 164 | 58 |
| A | 12.0 | 389 | 230 | 151 | 70 |
| B | 11.2 | 388 | 214 | 157 | 77 |

TABLE 5

Second Reactor Vent Gas Analysis

| Example No. | $O_2$ (mole %) | CO (mole %) | $CO_2$ (mole %) | HAC burn (lbs/Mlb PX) |
|---|---|---|---|---|
| 1 | 4.02 | 0.346 | 1.198 | 38.6 |
| 2 | 4.11 | 0.369 | 1.091 | 35.0 |
| 3 | 3.69 | 0.354 | 1.269 | 38.6 |
| 4 | 4.07 | 0.389 | 1.308 | 41.6 |
| 5 | 4.28 | 0.336 | 1.186 | 37.5 |
| 6 | 4.54 | 0.330 | 1.137 | 36.0 |
| 7 | 4.08 | 0.325 | 1.197 | 36.5 |
| 8 | 4.36 | 0.418 | 1.383 | 43.1 |
| 9 | 4.23 | 0.368 | 1.274 | 39.5 |
| 10 | 4.26 | 0.382 | 1.433 | 44.3 |
| 11 | 5.55 | 0.394 | 1.404 | 45.5 |
| 12 | 4.09 | 0.347 | 1.198 | 37.7 |
| 13 | 4.15 | 0.382 | 1.313 | 40.4 |
| 14 | 6.00 | 0.390 | 1.420 | 43.3 |
| 15 | 6.00 | 0.422 | 1.520 | 48.2 |
| 16 | 5.42 | 0.325 | 1.288 | 40.3 |
| 17 | 5.25 | 0.322 | 1.242 | 39.2 |
| 18 | 4.76 | 0.356 | 1.405 | 44.5 |
| A | 5.92 | 0.518 | 1.683 | 52.0 |
| B | 4.30 | 0.550 | 1.688 | 52.9 |

TABLE 6

Second Reactor Slurry Analysis

| Example No. | PX (ppmw) | HMBA (wt %) | 4CBA (wt %) | BA (wt %) | p-Toluic Acid (wt %) | p-Tolualdehyde (wt %) | TA conc (wt %) |
|---|---|---|---|---|---|---|---|
| 1 | 482 | 0.0115 | 0.3095 | 0.1218 | 0.5306 | 0.0585 | 37.1 |
| 2 | 328 | 0.0118 | 0.2817 | 0.1229 | 0.3970 | 0.0438 | 37.6 |
| 3 | 457 | 0.0153 | 0.3460 | 0.1253 | 0.5613 | 0.0614 | 33.9 |
| 4 | 388 | 0.0150 | 0.2826 | 0.1142 | 0.4608 | 0.0465 | 36.3 |
| 5 | 444 | 0.0118 | 0.3279 | 0.1162 | 0.5308 | 0.0507 | 37.5 |
| 6 | 392 | 0.0127 | 0.2944 | 0.1157 | 0.4680 | 0.0554 | 35.1 |
| 7 | 545 | 0.0131 | 0.3496 | 0.1131 | 0.6173 | 0.0646 | 33.9 |
| 8 | 456 | 0.0102 | 0.2312 | 0.1088 | 0.4078 | 0.0437 | 36.7 |
| 9 | 526 | 0.0114 | 0.2747 | 0.1116 | 0.5461 | 0.0710 | 35.3 |
| 10 | 406 | 0.0179 | 0.2748 | 0.1094 | 0.4313 | 0.0441 | 35.0 |
| 11 | 430 | 0.0090 | 0.2268 | 0.0917 | 0.3727 | 0.0338 | 33.3 |
| 12 | 532 | 0.0174 | 0.3434 | 0.1188 | 0.5888 | 0.0599 | 34.9 |
| 13 | 394 | 0.0145 | 0.2639 | 0.1118 | 0.4312 | 0.0447 | 37.1 |
| 14 | 501 | 0.0106 | 0.2409 | 0.1126 | 0.4353 | 0.0482 | 33.4 |
| 15 | 256 | 0.0086 | 0.2029 | 0.0922 | 0.2546 | 0.0247 | 33.2 |
| 16 | 281 | 0.0133 | 0.2385 | 0.1109 | 0.3443 | 0.0384 | 36.6 |
| 17 | 399 | 0.0076 | 0.1345 | 0.0566 | 0.2042 | 0.0227 | 37.5 |
| 18 | 401 | 0.0105 | 0.2759 | 0.1111 | 0.3737 | 0.0399 | 41.4 |
| A | 1449 | 0.0142 | 0.1889 | 0.0982 | 0.5250 | 0.1347 | 35.8 |
| B | 308 | 0.0100 | 0.2004 | 0.0983 | 0.2621 | 0.0242 | 38.1 |

TABLE 7

Recovered Product TA Analysis

| Example No. | Total HAC burn (sum of 2 reactors) (lbs/Mlb PX) | BA (ppmw) | 4-CBA (ppmw) | p-Toluic Acid (ppmw) | HMBA (ppmw) | OD 340 Washed & Filtered |
|---|---|---|---|---|---|---|
| 1 | 41 | 61 | 3684 | 619 | 72 | 0.501 |
| 2 | 37 | 54 | 3326 | 353 | 26 | 0.340 |
| 3 | 41 | 51 | 3993 | 515 | 64 | 0.399 |
| 4 | 44 | 50 | 3050 | 450 | 40 | 0.536 |
| 5 | 40 | 51 | 3569 | 542 | 64 | 0.509 |
| 6 | 38 | 49 | 3768 | 426 | 49 | 0.290 |
| 7 | 39 | 39 | 4244 | 617 | 106 | 0.372 |
| 8 | 46 | 44 | 2624 | 365 | 20 | 0.583 |
| 9 | 43 | 35 | 3236 | 511 | 46 | 0.563 |
| 10 | 47 | 31 | 3278 | 446 | 28 | 0.430 |
| 11 | 49 | 42 | 3032 | 51 | 21 | 0.480 |
| 12 | 41 | 54 | 4272 | 642 | 36 | 0.450 |
| 13 | 44 | 37 | 3103 | 345 | 22 | 0.354 |
| 14 | 49 | 39 | 2552 | 437 | 21 | 0.470 |
| 15 | 53 | 27 | 2436 | 248 | 10 | 0.287 |
| 16 | 44 | 36 | 3006 | 273 | 15 | 0.247 |
| 17 | 44 | 36 | 3404 | 335 | 41 | 0.334 |
| 18 | 48 | 49 | 3528 | 408 | 54 | 0.402 |
| A | 57 | 54 | 2224 | 499 | 40 | 1.790 |
| B | 57 | 50 | 2223 | 310 | 21 | 1.083 |

TABLE 8

Reactor Conditions

| | Comparative Example No. | | | | | | | | |
|---|---|---|---|---|---|---|---|---|---|
| | 1 | 2 | 3 | 4 | 5 | 6 | 7 | 8 | 9 |
| Feed Comp (wt. Fraction) | | | | | | | | | |
| PX | 0.253 | 0.255 | 0.255 | 0.256 | 0.255 | 0.255 | 0.256 | 0.255 | 0.253 |
| HAc | 0.712 | 0.709 | 0.710 | 0.710 | 0.710 | 0.709 | 0.710 | 0.710 | 0.713 |
| $H_2O$ | 0.032 | 0.032 | 0.032 | 0.032 | 0.032 | 0.032 | 0.032 | 0.032 | 0.032 |
| Liquid Feed Rate (lb/hr) | 10.5 | 10.5 | 10.5 | 10.5 | 8.7 | 10.5 | 8.7 | 10.5 | 8.7 |
| Temp. (° F.) | 387 | 387 | 387 | 387 | 386 | 386 | 388 | 387 | 387 |
| Pressure (psig) | 220 | 220 | 219 | 202 | 207 | 203 | 204 | 220 | 215 |
| Reactor Liquid Comp. | | | | | | | | | |
| Solvent Ratio (lb solv in reactor/lb PX fed) | 2.65 | 2.79 | 2.75 | 2.63 | 2.48 | 2.74 | 2.69 | 2.72 | 2.78 |
| Co in reactor liquid (ppmw) | 400 | 440 | 360 | 380 | 390 | 340 | 380 | 400 | 270 |
| Mn in reactor liquid (ppmw) | 380 | 410 | 320 | 350 | 380 | 460 | 320 | 360 | 240 |
| Br in reactor liquid (ppmw) | 470 | 520 | 430 | 450 | 460 | 600 | 410 | 470 | 340 |
| $H_2O$ (wt. %) | 11.2 | 11.6 | 11.0 | 10.3 | 11.6 | 11.1 | 11.1 | 11.1 | 11.2 |
| Air feed rate (SCFH) | 162 | 162 | 158 | 137 | 122 | 145 | 125 | 161 | 124 |
| Residence time (min.) | 82 | 77 | 75 | 77 | 129 | 75 | 122 | 80 | 122 |

TABLE 9

Vent Gas Analysis

| | Comparative Example No. | | | | | | | | |
|---|---|---|---|---|---|---|---|---|---|
| | 1 | 2 | 3 | 4 | 5 | 6 | 7 | 8 | 9 |
| $O_2$ (mole %) | 4.35 | 4.26 | 4.27 | 1.04 | 1.27 | 1.14 | 1.03 | 4.30 | 2.66 |
| CO (mole %) | 0.354 | 0.395 | 0.307 | 0.480 | 0.639 | 0.642 | 0.542 | 0.349 | 0.395 |
| $CO_2$ (mole %) | 1.226 | 1.314 | 1.085 | 1.330 | 1.786 | 1.334 | 1.541 | 1.157 | 1.366 |
| HAc burn (lbs/Mlb PX) | 45.9 | 48.9 | 38.8 | 42.2 | 60.7 | 48.6 | 53.0 | 43.0 | 46.1 |

TABLE 10

Reactor Slurry Analysis

| | Comparative Example No | | | | | | | | |
|---|---|---|---|---|---|---|---|---|---|
| | 1 | 2 | 3 | 4 | 5 | 6 | 7 | 8 | 9 |
| PX (ppmw) | 363 | 285 | 566 | 1224 | 231 | 518 | 392 | 334 | 554 |
| HMBA (wt %) | 0.0107 | 0.0113 | 0.0034 | 0.0297 | 0.0098 | 0.0178 | 0.0132 | 0.0094 | 0.0101 |
| 4CBA (wt %) | 0.2561 | 0.2178 | 0.3475 | 0.6271 | 0.1797 | 0.3664 | 0.3400 | 0.2376 | 0.3035 |
| BA (wt %) | 0.1334 | 0.1272 | 0.1415 | 0.1519 | 0.1327 | 0.1429 | 0.1649 | 0.1300 | 0.1509 |
| p-Toluic Acid (wt %) | 0.4393 | 0.3594 | 0.6657 | 1.3991 | 0.2639 | 0.6502 | 0.6255 | 0.4128 | 0.5355 |
| p-Tolualdehyde (wt %) | 0.0477 | 0.0397 | 0.0718 | 0.1599 | 0.0332 | 0.0982 | 0.0751 | 0.0540 | 0.0608 |
| TA conc. (wt %) | 37.0 | 37.1 | 37.9 | 39.3 | 40.4 | 38.9 | 40.1 | 36.4 | 37.1 |

TABLE 11

Recovered Product TA Analysis

| | Comparative Example No. | | | | | | | | |
|---|---|---|---|---|---|---|---|---|---|
| | 1 | 2 | 3 | 4 | 5 | 6 | 7 | 8 | 9 |
| BA (ppmw) | 58 | 51 | 42 | 74 | 65 | 81 | 83 | 50 | 58 |
| 4-CBA (ppmw) | 2751 | 2417 | 4057 | 8016 | 2265 | 5131 | 4200 | 2620 | 3461 |

TABLE 11-continued

Recovered Product TA Analysis

| | Comparative Example No. | | | | | | | | |
|---|---|---|---|---|---|---|---|---|---|
| | 1 | 2 | 3 | 4 | 5 | 6 | 7 | 8 | 9 |
| P-Toluic Acid (ppmw) | 412 | 396 | 659 | 1563 | 262 | 665 | 638 | 390 | 583 |
| HMBA (ppmw) | 29 | 16 | 43 | 207 | 32 | 142 | 96 | 40 | 44 |
| HAC burn (lbs/Mlb PX) (repeated here for comparison to Table 7) | 46 | 49 | 39 | 42 | 61 | 49 | 53 | 43 | 46 |
| OD 340 Washed and Filtered | 0.306 | 0.330 | 0.353 | 1.918 | 1.019 | 2.677 | 1.248 | 0.292 | 0.528 | color OD 340 (0.34 and 0.29) and acetic acid burn (37 and 38 lbs/M lb PX) are both acceptable.

From the above description, it is apparent that the goals of the present invention have been achieved. While only certain embodiments have been set forth, alternative embodiments and various modifications will be apparent from the above description to those skilled in the art. These and other alternatives are considered equivalents and within the spirit and scope of the present invention.

The invention claimed is:

1. A continuous staged countercurrent process that obtains improved oxygen utilization and desirable product quality for the catalytic oxidation of at least one benzene disubstituted with oxidizable substituents selected from the class consisting of alkyl, hydroxyalkyl, aldehyde, carboxy groups and mixtures thereof, to its corresponding dicarboxylic acid in a solvent system, comprising the steps of:

(a) introducing into a first oxidation stage a feed mixture comprising at least a portion of the total amount of each of (i) the solvent comprising an organic acid, (ii) at least one catalytic metal selected from the class consisting of manganese, cobalt, nickel, zirconium, hafnium, cerium and mixtures thereof, and (iii) bromine at a mole ratio based on total catalytic metals within the range of from about 1:20 to about 5:1, and from about 7 to about 60 weight percent of the total amount of the at least one disubstituted benzene introduced into the first oxidation stage and into a second oxidation stage;

(b) partially oxidizing the at least one disubstituted benzene in the first oxidation stage with the presence of a molecular oxygen-containing gas initially containing from about 3 to about 20 volume percent of molecular oxygen, at a temperature in the range of from about 250° F. to about 401° F. and with the relative amounts of disubstituted benzene, catalytic metal, solvent and bromine and with the temperature being such that from about 25 to about 99.95 weight percent of the disubstituted benzene fed to the first oxidation stage is oxidized to form a gas mixture comprising unreacted molecular oxygen and vaporized solvent and a first product mixture comprising dicarboxylic acid product, partially oxidized disubstituted benzene and unreacted disubstituted benzene and solvent, and at a pressure in the range of from about 130 to about 215 psig to maintain the disubstituted benzene, partially oxidized disubstituted benzene, dicarboxylic acid product and solvent as a liquid or solid-liquid slurry, and such that the concentration of residual molecular oxygen in the remaining gas mixture is from about 0.3 to about 2 volume percent thereby obtaining improved oxygen utilization;

(c) recovering the resulting first product mixture from the first oxidation stage and feeding at least a portion of the recovered first product mixture to the second oxidation stage;

(d) removing the remaining gas mixture from the first oxidation stage and partially condensing the gas mixture so as to remove therefrom condensable solvent and at least a portion of the condensed solvent is introduced into the first oxidation stage, the second oxidation stage, or both thereof;

(e) feeding to the second oxidation stage a gas containing molecular oxygen and the portion not fed into the first oxidation stage, if any, of the aforesaid total amounts introduced in steps (a) and (e) of disubstituted benzene, catalytic metal, solvent and bromine;

(f) oxidizing in the second oxidation stage the partially oxidized disubstituted benzene and unreacted disubstituted benzene fed to the second oxidation stage with a molecular oxygen-containing gas containing from about 15 to about 50 volume percent of molecular oxygen at a temperature within the range of from about 347° F. to about 421° F., and with the relative amounts of disubstituted benzene, partially oxidized disubstituted benzene, catalytic metal, solvent and bromine and with the temperature being such that from about 96 to about 100 weight percent of the disubstituted benzene and partially oxidized disubstituted benzene are oxidized to form a gas mixture comprising unreacted molecular oxygen and vaporized solvent and a second product mixture comprising the dicarboxylic acid product and solvent, and at a pressure in the range of from about 170 to about 235 psig to maintain the dicarboxylic acid product, partially oxidized disubstituted benzene and unreacted disubstituted benzene as a liquid or solid-liquid slurry and such that the concentration of residual molecular oxygen in the remaining gas mixture is in the range of from about 3 to about 15 volume percent;

(g) recovering from the second oxidation stage the second product mixture comprising the dicarboxylic acid product having an optical density at 340 nm of less than 1.0; and (h) withdrawing from the second oxidation stage and recycling to the first oxidation stage the residual molecular oxygen containing gas.

2. The process of claim 1 wherein the disubstituted benzene is para-disubstituted benzene and the corresponding dicarboxylic acid is terephthalic acid.

3. The process of claim 2 wherein the substituents in the para-disubstituted benzene are alkyl groups having from one to four carbon atoms.

4. The process of claim 1 wherein the solvent comprises acetic acid.

5. The process of claim 1 wherein the catalytic metals are cobalt and manganese.

6. The process of claim 1 wherein the atom ratio of manganese to cobalt in the reaction mixture in the first oxidation stage is in the range of from about 1:100 to about 100:1.

7. The process of claim 1 wherein the reaction mixture in the first oxidation stage mixture comprises a mole ratio of bromine-to-total catalytic metals therein of from about 1:5 to about 2:1.

8. The process of claim 1 wherein the temperature in the first oxidation stage is maintained within the range of from about 277° F. to about 351° F.

9. The process of claim 1 wherein the molecular oxygen-containing gas introduced in the first oxidation stage contains from about 3 to about 11 volume percent of molecular oxygen.

10. The process of claim 1 wherein the concentration of residual molecular oxygen in the gas removed from the first oxidation stage is less than about 1 volume percent.

11. The process of claim 1 wherein the degree of conversion of the disubstituted benzene to partially oxidized disubstituted benzene and dicarboxylic acid thereof in the first oxidation stage is within the range of from about 60 to about 99.95 weight percent.

12. The process of claim 1 wherein the molecular oxygen-containing gas introduced into the second oxidation stage contains from about 20 to about 25 volume percent of molecular oxygen.

13. The process of claim 1 wherein the concentration of residual molecular oxygen in the gas removed from the second oxidation stage is from about 3 to about 11 volume percent.

14. The process of claim 13 wherein the concentration of residual molecular oxygen in the gas removed from the second oxidation stage is from about 3 to about 8 volume percent.

15. The process of claim 1 wherein the degree of conversion of the disubstituted benzene and partially oxidized disubstituted benzene to the dicarboxylic acid thereof in the second oxidation stage is within the range of from about 97 to about 100 weight percent.

16. The process of claim 5 wherein from about 20 to about 100 weight percent of the aforesaid total amount of manganese added in steps (a) and (d) is added in the first oxidation stage.

17. The process of claim 5 wherein from about 20 to about 100 weight percent of the aforesaid total amount of cobalt added is added in steps (a) and (d) in the first oxidation stage.

18. The process of claim 1 wherein from about 20 to about 100 weight percent of the total aforesaid amount of bromine added in steps (a) and (d) is added in the first oxidation stage.

19. The process of claim 1 wherein from about 15 to about 35 weight percent of the aforesaid total amount of disubstituted benzene added in steps (a) and (d) is added in the first oxidation stage.

20. The process of claim 1 wherein from about 10 to about 100 weight percent of the total aforesaid amount of solvent added in steps (a) and (d) is added in the first oxidation stage.

21. The process of claim 1 wherein the temperature in the first oxidation stage is at least 5.5° F. lower than the temperature in the second oxidation stage.

22. The process of claim 1 wherein the condensed solvent is introduced into the second oxidation stage.

23. The process of claim 1 wherein the second product mixture recovered from the second oxidation stage is subjected to oxidation conditions in a third oxidation stage to thereby oxidize oxidizable impurities therein.

24. The process of claim 23 wherein the oxidized impurities are separated from the dicarboxylic acid product to thereby produce a purified dicarboxylic acid product.

* * * * *